United States Patent [19]

Biller

[11] Patent Number: 5,332,728
[45] Date of Patent: Jul. 26, 1994

[54] METHOD FOR TREATING A FUNGAL INFECTION

[75] Inventor: Scott A. Biller, Ewing, N.J.

[73] Assignee: Bristol-Myers Squibb Company, Princeton, N.J.

[21] Appl. No.: 980,417

[22] Filed: Nov. 23, 1992

[51] Int. Cl.$^5$ ............................................. A61K 31/66
[52] U.S. Cl. .................... 514/107; 514/95; 514/102; 514/108
[58] Field of Search .................. 514/107, 95, 102, 108

[56] References Cited

U.S. PATENT DOCUMENTS

| | | | |
|---|---|---|---|
| 3,518,200 | 6/1970 | Fitch et al. | 660/912 |
| 3,609,075 | 9/1971 | Barbera | 680/625 |
| 5,026,554 | 6/1991 | Bartizal et al. | 424/404 |
| 5,053,425 | 10/1991 | Bartizal et al. | 514/452 |
| 5,055,487 | 10/1991 | Bartizal et al. | 514/452 |
| 5,102,907 | 4/1992 | Bergstrom et al. | 514/456 |
| 5,157,027 | 10/1992 | Biller et al. | 514/107 |

FOREIGN PATENT DOCUMENTS

| | | |
|---|---|---|
| 38764 | 10/1981 | European Pat. Off. |
| 100718 | 2/1984 | European Pat. Off. |
| 324421 | 7/1989 | European Pat. Off. |
| 339237 | 11/1989 | European Pat. Off. |
| 356866 | 3/1990 | European Pat. Off. |
| 409181 | 1/1991 | European Pat. Off. |
| 448393 | 9/1991 | European Pat. Off. |
| 0494622A1 | 2/1992 | European Pat. Off. |
| 0503520A1 | 9/1992 | European Pat. Off. |
| WO9212156 | 7/1992 | PCT Int'l Appl. |
| WO9212157 | 7/1992 | PCT Int'l Appl. |
| WO9212158 | 7/1992 | PCT Int'l Appl. |
| WO9212159 | 7/1992 | PCT Int'l Appl. |
| WO9212160 | 7/1992 | PCT Int'l Appl. |
| WO9216530 | 10/1992 | PCT Int'l Appl. |

OTHER PUBLICATIONS

Hutchinson, D. et al J. Organomet. Chem. 291(2) 145-51 1985.

Baxter, A. et al, "Squalestin 1, a Potent Inhibitor of Squalene Synthase, Which Lowers Serum Cholesterol in Vivo" Journal of Biological Chemistry, vol. 267, No. 17, pp. 11705-11708, 1992.

Dawson, M. J., "The Squalestatins, Novel Inhibitors of Squalene Synthase Produced by a Species of Phoma" The Journal of Antibiotics, vol. 45 No. 5, pp. 639-658, May 1992.

*Primary Examiner*—Paul J. Killos
*Attorney, Agent, or Firm*—Burton Rodney

[57] ABSTRACT

A method is provided for treating a fungal infection which includes the step of administering a therapeutically effective amount of a phosphorus-containing squalene synthetase inhibitor.

20 Claims, No Drawings

METHOD FOR TREATING A FUNGAL INFECTION

FIELD OF THE INVENTION

The present invention relates to a method for treating a fungal infection by administering a therapeutic amount of a bisphosphonate, α-phosphonosulfonate or phosphinylformic acid.

BACKGROUND OF THE INVENTION

U.S. Pat. No. 5,026,554 to Bartizal et al discloses a method of inhibiting fungal growth using a non-phosphorus containing inhibitor of squalene synthetase having the structure

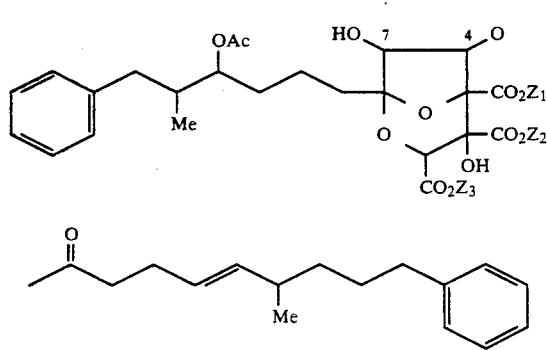

wherein $Z_1$, $Z_2$ and $Z_3$ are each independently selected from:

(a) H;
(b) $C_{1-3}$alkyl;
(c) $C_{1-3}$alkyl substituted with a member of the group consisting of:
  (i) phenyl,
  (ii) phenyl substituted with methyl, ethoxy, halogen (Cl, Br, F, I) or hydroxy; or a pharmaceutically acceptable salt of a compound of the above formula.

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling. H. C., in "Biosynthesis of Isoprenoid Compounds," Vol. I, Chapter 8, pp. 413-441, J. Wiley and Sons, 1981, and references therein). This enzyme is the first committed step of the de novo cholesterol biosynthetic pathway.

Squalene synthetase inhibitors which block the action of squalene synthetase (after the formation of farnesyl pyrophosphate) are disclosed in U.S. Pat. Nos. 4,871,721 and 5,025,003, U.S. application Ser. No. 501,204, filed Mar. 29, 1990, U.S. application Ser. No. 699,429, filed May 13, 1991, and U.S. application Ser. No. 07/967,904, filed Oct. 28, 1992, now abandoned which discloses α-phosphonosulfonate squalene synthetase inhibitors.

DESCRIPTION OF THE INVENTION

In accordance with the present invention, it has been found that fungal growth may be inhibited by administering an anti-fungal amount of a phosphorus-containing compound which is preferably a bisphosphonate, α-phosphonosulfonate or phosphinylformic acid.

Bisphosphonates suitable for use herein include compounds disclosed in U.S. application Ser. No. 699,429 filed May 13, 1991, by Billet et al which have the following structure

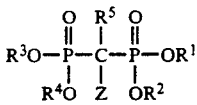

wherein $R^1$, $R^2$, $R^3$ and $R^4$ are the same or different and are H, alkyl, a metal ion or a prodrug ester;

$R^5$ is H, halogen or lower alkyl;

Z a lipophilic group containing at least 6 carbons and can be substituted alkenyl wherein the alkenyl group contains from 7 to 25 carbon atoms in the chain and from 1 to 4 double bonds; substituted alkynyl containing 1 to 4 triple bonds; mixed alkenyl-alkynyl containing 1 to 3 double bonds and 1 to 3 triple bonds and wherein alkenyl and/or alkynyl may be substituted or unsubstituted; or a substituted phenylalkyl group of the structure

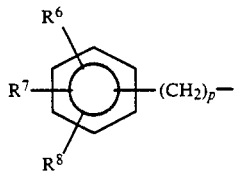

wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryloxy, hydroxy, halogen, nitro, amino, thiol, alkylthio, arylthio, alkyl-sulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino, at least one of $R^6$, $R^7$ and $R^8$ being alkenyl, alkenyloxy, alkynyl or alkynyl-oxy; and wherein the total number of carbons in the substituted phenylalkyl group exceeds 10 carbons.

The terms "substituted alkenyl" and "substituted alkynyl" as employed herein with respect to Z refers to alkenyl or alkynyl substituted with 1 to 4 groups which may be alkyl, alkenyl, alkeynyl, halogen, hydroxy, alkoxy, alkenyloxy, alkynyloxy, aryl and/or cycloalkyl.

The $(CH_2)_p$ group may contain one or more alkyl, alkoxy, alkenyl, alkynyl, hydroxy and/or halogen substituents.

Preferred embodiments of formula I bisphosphonates have the structure

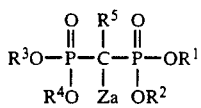

wherein $R^1$, $R^2$, $R^3$, $R^4$ and $R^5$ are as defined above and Za is substituted alkenyl which includes from 1 to 4 double bonds and is substituted with from 1 to 4 alkyl groups.

In addition, other bisphosphonates suitable for use herein and disclosed in application Ser. No. 699,429 have the structure

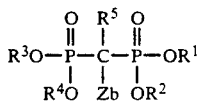

wherein Zb is

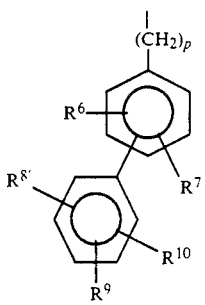

wherein $R^1$, $R^2$, $R^3$, $R^4$, $R^5$, $R^6$, $R^7$ and $(CH_2)_p$ are as defined hereinbefore, except that $R^6$ and $R^7$ may be any one of the groups included under the definition $R^6$ and $R^7$, set out hereinbefore without limitation; $R^{8'}$, $R^9$ and $R^{10}$ are the same or different and are as defined hereinbefore with respect to $R^6$ and $R^7$, without limitation.

Preferred are compounds of formula III wherein the $R^{8'}$, $R^9$, $R^{10}$-substituted phenyl is para to the $R^6$, $R^7$-phenylene. These compounds have been found to inhibit cholesterol biosynthesis when administered orally.

In another embodiment of the present invention, bisphosphonates (disclosed in Ser. No. 699,429) may be employed which have the structure

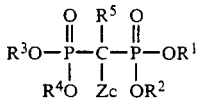

wherein $R^1$, $R^2$, $R^3$, $R^4$ and $R^5$ are as defined hereinbefore and Zc is alkyl wherein the alkyl group contains from 9 to 14 carbons in the normal chain and is substituted with 1, 2, 3 or 4 alkyl groups.

Still another embodiment of bisphosphonate compounds (disclosed in Ser. No. 699,429) have the structure

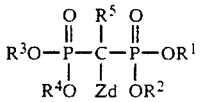

wherein Zd is

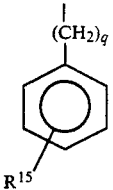

wherein $R^1$, $R^2$, $R^3$, $R^4$ and $R^5$ are as defined hereinbefore and $(CH_2)_q$ contains at least 2 carbons in the chain and may include 0, 1, 2 or 3 double bonds and/or 0, 1, 2 or 3 triple bonds in the normal chain, preferably 3 to 7 carbons in the normal chain, and may include one or more alkyl, alkenyl, alkynyl, alkoxy, hydroxy and/or halogen substituents; and $R^{15}$ is alkyl containing from 2 to 20 carbons, and preferably is in the para position, and the total number of carbons in Zd exceeds 10.

Other bisphosphonates suitable for use herein are compounds disclosed in U.S. application Ser. No. 501,204 filed Mar. 29, 1990, by Billet et al and have the following structure

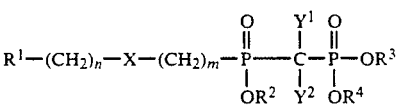

wherein m is 0, 1, 2 or 3; n is 0, 1, 2, 3 or 4; $Y^1$ and $Y^2$ are H or halogen preferably H or F; $R^2$, $R^3$ and $R^4$ are independently H, metal ion, $C_1$ to $C_8$ alkyl or $C_3$ to $C_{12}$ alkenyl; X is O, NH,

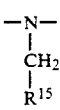

or S (wherein $R^{15}$ is H or $C_1$ to $C_5$ alkyl); $R^1$ is $R^5$—$Q^1$—$Q^2$—$Q^3$— wherein $Q^1$, $Q^2$ and $Q^3$ are independently:

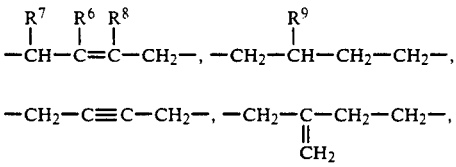

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); R is H, halogen, lower alkyl or alkylthio; $R^8$ is H, halogen, trimethylsilyl or lower alkyl; $R^9$ is H, or lower alkyl; $R^5$ is

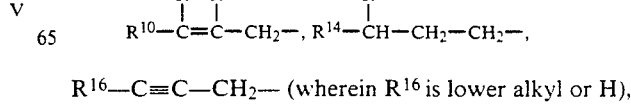

$R^{16}$—C≡C—$CH_2$— (wherein $R^{16}$ is lower alkyl or H),

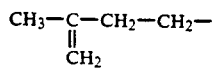

or $CH_3(CH_2)_p-$ where p is 2 to 7;

$R$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the provisos that if all of $Q^1$, $Q^2$ and $Q^3$ are bonds, then $R^{10}$ and $R^{11}$ cannot both be H, and $R^5$ cannot be $CH_3(CH_2)_p-$, with $p \leq 4$; if m is o, X is other than S; and if m is o and X is O, then n is 1, 2, 3 or 4, including all stereoisomers thereof.

The term "lower alkenyl" or "alkenyl" as used above by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

Preferred are those compounds of formula VI which have the following formula:
VII

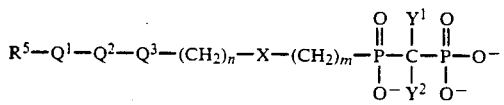

wherein $R^5$ is

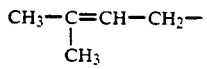

$Q^3$ is a bond;
$Q^2$ is

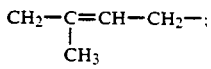

$-CH_2-C\equiv C-CH_2-$;  or  $-CH_2-CH=CH-CH_2-$;
$Q^1$ is

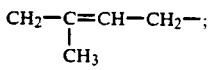

n is 0 or 1; m is 1 or 2; X is O and $Y^1$ and $Y^2$ are each H or F, in the form of the salts or acid.

In addition, preferred are those compounds of formula VI which have the following structure
VIA-A

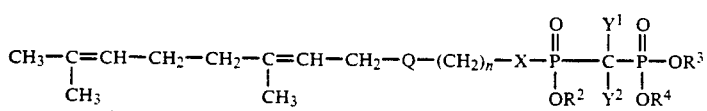

wherein Q is

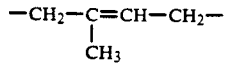

or a bond; n is 1 or 2; X is O, $Y^1$ and $Y^2$ are each H or each F; $R^2$, $R^3$ and $R^4$ are alkyl, H or metal ions; or X is NH and n is 0.

In addition, phosphinylformic acids which may be employed herein include compounds disclosed in U.S. Pat. No. 5,025,003 to Billet and have the following structure

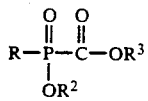
VIII wherein $R^2$ is a metal ion, lower alkyl or H;
$R^3$ is a metal ion or lower alkyl;
R is $R^1-(CH_2)_n-$, $R^1-(CH_2)_mO-$ or $R^1-(CH_2)_mOCH_2-$, wherein n is 1 to 4, m is 0 to 3; and $R^1$ is $R^5-Q^1-Q^2-Q^3-$ wherein $Q^1$, $Q^2$ and $Q^3$ are independently:

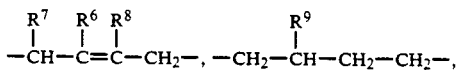

$-CH_2-C\equiv C-CH_2-$, or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, fluoro or fluoroalkyl (e.g., $CH_2F$, $CF_3$); $R^7$ is H, fluoro, lower alkyl or alkylthio; $R^8$ is H, fluoro, trimethylsilyl or lower alkyl; $R^9$ is H, or lower alkyl; $R^5$ is

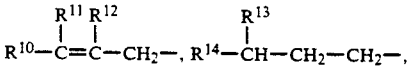

$R^{16}-C\equiv C-CH_2-$ (wherein $R^{16}$ is lower alkyl or H), or $CH_3(CH_2)_p-$ where p is 2 to 7; $R^{10}$ and $R^{11}$ are independently hydrogen, lower alkyl such as methyl or ethyl, fluoro, lower alkenyl or fluoroalkyl or $R^{10}$ and $R^{11}$ can be taken together to form $(CH_2)_s$, where s is 2 to 7; $R^{12}$ is hydrogen, lower alkyl, fluoro or lower alkenyl; $R^{13}$ and $R^{14}$ are independently lower alkyl such as methyl or ethyl; with the proviso that if all of $Q^1$, $Q^2$ and $Q^3$ are bonds, then $R^{10}$ and $R^{11}$ cannot both be H, and $R^5$ cannot be $CH_3(CH_2)_p$, with p<4, including all stereoisomers thereof.

The term "lower alkenyl" or "alkenyl" as used herein is defined hereinbefore.

Preferred are those compounds of formula VIII wherein $R^1$ is

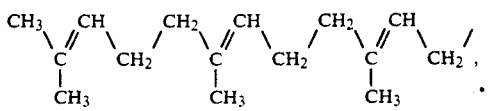

n is 1, 2 or 3, m is 1 or 2, $R^2$ is H or a metal ion, and $R^3$ is lower alkyl, a metal ion or H.

Other bisphosphonates suitable for use herein include compounds disclosed in U.S. Pat. No. 4,871,721 to Biller and have the following structure:

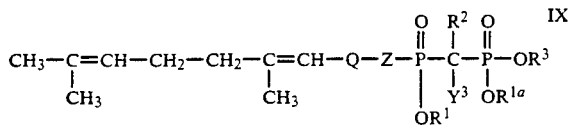

wherein Q is

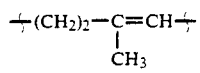

or a bond;

Z is —$(CH_2)_n$— or —$(CH_2)_p$—CH=CH—$(CH_2)_m$, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

Preferred are those compounds of formula IX which have the following structure
IXA

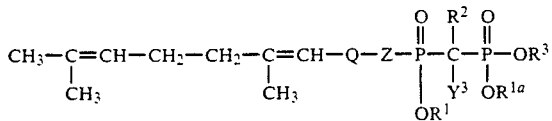

wherein Q is,

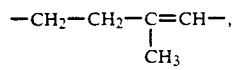

Z is —$CH_2CH_2$— or —CH=CH—; $R^2$ and $R^3$ are each H or each F; R, $R^1$ and $R^{1a}$ are OH or metal ions.

α-Phosphonosulfonate compounds suitable for use herein are disclosed in U.S. application Ser. No. 07/967,904, filed Oct. 28, 1992, now abandoned and have the following structure

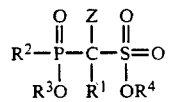

wherein $R^2$ is $OR^5$ or $R^{5a}$, $R^3$ and $R^5$ are the same or different and are H, alkyl, arylalkyl, aryl, cycloalkyl, a metal ion or other pharmaceutically acceptable cations as defined below, or a prodrug ester;

$R^{5a}$ is H, alkyl, arylalkyl or aryl;

$R^4$ is H, alkyl, cycloalkyl, aryl, aryl-alkyl, metal ion or other pharmaceutically acceptable cations as defined below, or a prodrug ester;

Z is H, halogen, lower alkyl or lower alkenyl;

$R^1$ a lipophilic group containing at least 7 carbons and is alkyl containing 7 to 25 carbons in the chain; alkenyl containing from 7 to 25 carbon atoms in the chain and from 1 to 6 double bonds; alkynyl containing 1 to 6 triple bonds; mixed alkenyl-alkynyl containing 1 to 5 double bonds and 1 to 5 triple bonds; and where in the above groups alkenyl and/or alkynyl may be substituted or unsubstituted; cycloalkyl; cycloheteroalkyl linked through a carbon on the ring or a heteroatom; aryl; heteroaryl; heteroarylalkyl; cycloalkylalkyl; cycloheteroalkylalkyl; or a group of the structure

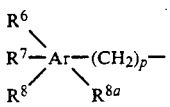

wherein Ar is aryl (such as phenyl or naphthyl), heteroaryl (5 or 6 membered) and may include one to three additional rings fused to Ar (such as aryl, cycloalkyl, heteroaryl or cycloheteroalkyl) and wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, preferably from 3 to 25 carbons, alkoxy containing 1 to 40 carbons, preferably from 3 to 25 carbons, alkenyl containing 2 to 40 carbons, preferably from 3 to 25 carbons, alkenyloxy containing 2 to 40 carbons, preferably from 3 to 25 carbons, alkynyl containing 2 to 40 carbons, preferably from 3 to 25 carbons, alkynyloxy containing 2 to 40 carbons, preferably from 3 to 25 carbons, cycloheteroalkyl, cycloheteroalkylalkyl, heteroaryl, cycloalkyl, cycloalkylalkyl, Ar-alkyl, (such as arylalkyl), ArO (such as aryloxy), Ar-amino (such as arylamino), hydroxy, halogen, nitro, Ar (such as aryl), amino, substituted amino wherein the amino includes 1 or 2 substituents (which are alkyl, alkenyl, aryl or any of the Ar groups mentioned above), thiol, alkylthio, Ar-thio (such as arylthio), alkyl-sulfinyl, Ar-sulfinyl (such as arylsulfinyl), alkylsulfonyl, Ar-sulfonyl (such as arylsulfonyl), carboxy, cyano, alkoxycarbonyl, aminocarbonyl, alkylcarbonyloxy, Ar-carbonyloxy (such as arylcarbonyloxy), Ar-carbonylamino (such as arylcarbonylamino) or alkylcarbonylamino, as well as any of the Ar groups as defined above, and preferably wherein the total number of carbons in the substituted Ar—$(CH_2)_p$— group exceeds 10 carbons; including pharmaceutically acceptable salts thereof such as alkali metal salts such as lithium, sodium or potassium, alkaline earth metal salts such as calcium or magnesium, as well as zinc or aluminum and other FDA approved cations such as ammonium, choline, diethanolamine, ethylenediamine, and salts of naturally occuring amino acids such as arginine, lysine, alanine and the like.

The $(CH_2)_p$ group may contain 1, 2, 3 or more alkyl, alkoxy, alkenyl, alkynyl, hydroxy and/or halogen substituents as well as any of the substituents defined for $R^6$.

Thus, the α-phosphonosulfonates suitable for use herein include the following sub-genuses:
XA

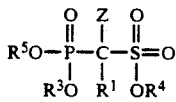

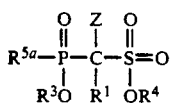

Preferred are compounds of formulae X and XA wherein $R^2$ is $OR^5$ and $R^5$ is a metal ion such as Na or K, or H or a pharmaceutically acceptable salt and especially prodrug esters as disclosed;

$R^3$ is H, a metal ion such as Na or K;

$R^4$ is a metal ion such as Na or K;

$R^1$ is alkenyl such as

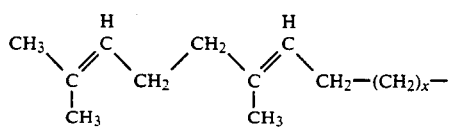

wherein $(CH_2)_x$ is defined as $(CH_2)_p$ above and $x$ is preferably 2 to 8,

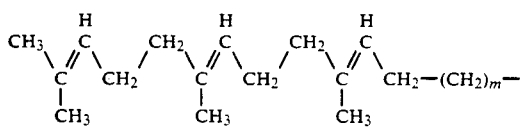

m is 1 to 5;

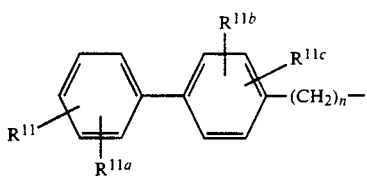

n = 1 to 15;

$R^{11}$, $R^{11a}$, $R^{11b}$, and $R^{11c}$ are independently selected from H, alkyl such as propyl, alkoxy, such as methoxy or propyloxy, alkenyl such as

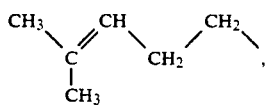

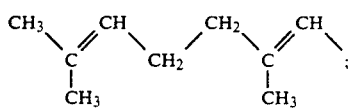

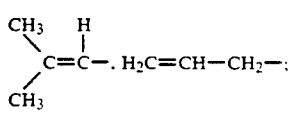

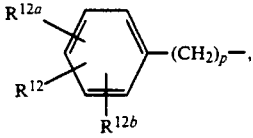

wherein $R^{12}$, $R^{12a}$ and $R^{12b}$ are independently selected from H, aryl (such as phenyl or naphthyl), alkylphenyl (such as p-propylphenyl, p-pentylphenyl), alkyl containing 1 to 20 carbons (such as p-heptyl), halo, alkoxy (such as methoxy or propyloxy), alkenyl (such as

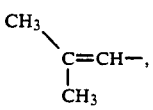

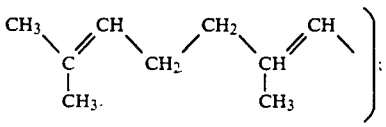

arylalkyloxy (such as phenethyloxy), alkenyloxy (such as

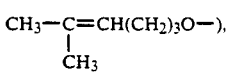

aryloxy (such as phenoxy), phenylalkyl (such as benzyl, phenylpropyl), alkylphenoxy (such as orthobutylphenoxy), alkenylphenyl (such as

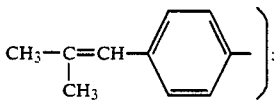

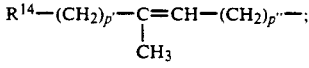

or

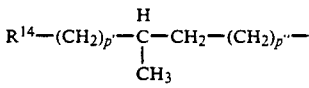

wherein $R^{14}$ is aryl, heteroaryl, aryloxy, heteroaryloxy, cycloalkyl, heterocycloalkyl, and $(CH_2)_{p'}$ and $(CH_2)_{p''}$ are as defined above for $—(CH_2)_p—$. Preferred p' and p" are independently 1 to 4;

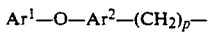

wherein $Ar^1$ and $Ar^2$ are independently selected from any of the Ar groups defined hereinbefore, and $(CH_2)_p$ is as defined hereinbefore.

Of all the phosphorus containing compounds disclosed herein, the α-phosphonosulfonates are most preferred.

Another embodiment of bisphosphonate compounds which may be employed are hydroxyphosphinyl phosphonates (disclosed in U.S. application Ser. No. 950,555, filed Sep. 25, 1992), which have the structure

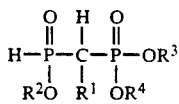

XII wherein $R^2$, $R^3$ and $R^4$, are independently H, alkyl, a metal ion or a prodrug ester; and $R^1$ is a lipophilic group containing at least 6 carbons, and including pharmaceutically acceptable salts thereof, wherein $R^1$ is alkyl, alkenyl, alkynyl or aryl.

$R^1$ can be alkenyl containing from 7 to 25 carbon atoms in the chain and from 1 to 4 double bonds; alkynyl containing 1 to 4 triple bonds; mixed alkenyl-alkynyl containing 1 to 3 double bonds and 1 to 3 triple bonds, and where in the above groups alkyl, alkenyl and/or alkynyl may be substituted or unsubstituted; or a group of the structure

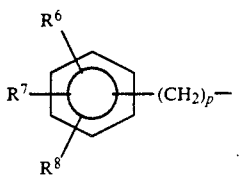

wherein $(CH_2)_p$ contains from 1 to 15 carbons in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, aryl, aryloxy, hydroxy, halogen, nitro, amino, thiol, alkylthio, arylthio, alkylsulfinyl, arylsulfinyl, alkyl-sulfonyl, arylsulfonyl, carboxy, alkoxycarbonyl, aminocarbonyl, alkylcarbonyloxy, arylcarbon-yloxy, arylcarbonylamino or alkylcarbonylamino.

The disclosures of the above U.S. patents and U.S. patent applications are incorporated herein by reference. The preferred compounds in these patents and patent applications are the preferred compounds for use in the method of the invention.

In carrying out the method of the invention, a pharmaceutical composition will be employed containing at least one phosphorus containing squalene synthetase inhibitor in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1-4 times per day.

A typical capsule for oral administration contains protein-prenyl transferase inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of sterile protein-prenyl transferase inhibitor into a vial, aseptically freeze-drying and sealing. For use, the contents of the vial are mixed with 2 mL of physiological saline, to produce an injectable preparation.

What is claimed is:

1. A method for treating a fungal infection, which comprises administering to a mammalian species in need of treatment a therapeutically effective amount of a phosphorus containing squalene synthetase inhibitor, wherein the squalene synthetase inhibitor is a bisphosphonate, α-phosphonosulfonate or a phosphinylformic acid.

2. The method as defined in claim 1, wherein the squalene synthetase inhibitor is a α-phosphonosulfonate.

3. The method as defined in claim 1, wherein the squalene synthetase inhibitor has the structure

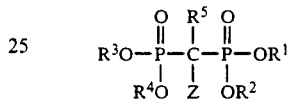

wherein $R^1$ $R^2$ $R^3$ and $R^4$ are the same or different and are H, lower alkyl, a metal ion or a prodrug ester;

$R^5$ is H, halogen or lower alkyl;

Z is substituted alkenyl wherein the alkenyl group contains at least 7 carbon atoms in the chain and from 1 to 4 double bonds; substituted alkynyl containing 1 to 4 triple bonds; mixed alkenylalkynyl containing 1 to 3 double bonds and 1 to 3 triple bonds, and wherein alkenyl and/or alkynyl may be substituted or unsubstituted; or a substituted phenylalkyl group of the structure

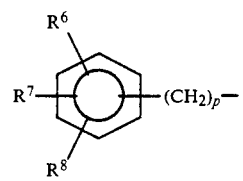

wherein $(CH_2)_p$ contains from 1 to 15 carbons in the chain and may include 0, 1, 2 or 3 double bonds and/or 0, 1, 2 or 3 triple bonds in the normal chain and/or may include 0, 1, 2 or 3 substituents which are alkyl, alkenyl, alkoxy, alkynyl, hydroxy and/or halogen; and $R^6$ $R^7$ and $R^8$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino, at least one of $R^6$, $R^7$ and $R^8$ being alkenyl alkenyloxy, alkynyl or alkynyloxy, and wherein the total number of carbons in $$\begin{array}{c} R^6 \\ | \\ R^7 - \text{[benzene ring]} - (CH_2)_p - \\ | \\ R^8 \end{array}$$

exceeds 10 carbons.

4. The method as defined in claim 3 wherein Z is substituted alkenyl or substituted alkynyl.

5. The method as defined in claim 1, wherein the squalene synthetase inhibitor has the structure $$\begin{array}{c} O \quad R^5 \quad O \\ \| \quad | \quad \| \\ R^3O-P-C-P-OR^1 \\ | \quad | \quad | \\ R^4O \quad Za \quad OR^2 \end{array}$$

wherein $R^1$, $R^2$, $R^3$ and $R^4$ are the same or different and are H, alkyl, a metal ion or a prodrug ester; $R^5$ is H, halogen or alkyl, and Za is substituted alkenyl which includes 1 to 4 double bonds and is substituted with from 1 to 4 lower alkyl groups.

6. The method as defined claim 1, wherein the squalene synthetase inhibitor has the structure $$\begin{array}{c} O \quad R^5 \quad O \\ \| \quad | \quad \| \\ R^3O-P-C-P-OR^1 \\ | \quad | \quad | \\ R^4O \quad Zb \quad OR^2 \end{array}$$

wherein Zb is $$\begin{array}{c} | \\ (CH_2)_p \\ R^6 - \text{[benzene]} - R^7 \\ R^{8'} \\ R^9 - \text{[benzene]} - R^{10} \end{array}$$

$R^1$, $R^2$, $R^3$ and $R^4$ are the same or different and are H, alkyl, a metal ion or a prodrug ester;

$R^5$ is H, halogen or alkyl;

p is 1 to 15;

$(CH_2)_p$ may include 0, 1, 2 or 3 double bonds and/or 0, 1, 2 or 3 triple bonds in the normal chain, and/or may include 0, 1, 2 or 3 substituents which are alkyl, alkoxy, alkenyl, alkynyl, hydroxy and/or halogen; and $R^6$, $R^7$, $R^{8'}$, $R^9$ and $R^{10}$ are the same or different and are H, alkyl containing 1 to 40 carbons, alkoxy containing 1 to 40 carbons, alkenyl containing 2 to 40 carbons, alkenyloxy containing 2 to 40 carbons, hydroxy, alkynyl containing 2 to 40 carbons, alkynyloxy containing 2 to 40 carbons, aryloxy, halogen, nitro, amino, thio, alkylthio, arylthio, arylsulfinyl, alkylsulfinyl, arylsulfonyl, alkylsulfonyl, carboxy, alkylcarbonyloxy, arylcarbonyloxy, alkoxycarbonyl, aminocarbonyl, arylcarbonylamino or alkylcarbonylamino.

7. The method as defined in claim 1, wherein the squalene synthetase inhibitor has the structure $$\begin{array}{c} O \quad R^5 \quad O \\ \| \quad | \quad \| \\ R^3O-P-C-P-OR^1 \\ | \quad | \quad | \\ R^4O \quad Zc \quad OR^2 \end{array}$$

wherein Zc is substituted alkyl containing from 9 to 14 carbons in the normal chain and is substituted with 1 to 4 lower alkyl groups;

$R^1 R^2 R^3$ and $R^4$ are the same or different and are H, alkyl, a metal ion or a prodrug ester; and $R^5$ is H, halogen or alkyl.

8. The method as defined in claim 1, wherein the squalene synthetase inhibitor has the structure $$\begin{array}{c} O \quad R^5 \quad O \\ \| \quad | \quad \| \\ R^3O-P-C-P-OR^1 \\ | \quad | \quad | \\ R^4O \quad Zb \quad OR^2 \end{array}$$

wherein Zd is $$\begin{array}{c} | \\ (CH_2)_q \\ \text{[benzene ring]} \\ R^{15} \end{array}$$

q is 2 to 15, $(CH_2)q$ may include 0, 1, 2 or 3 double bonds and/or 0, 1, 2 or 3 triple bonds in the normal chain and may optionally include one or more alkyl, alkenyl, alkynyl, hydroxy, alkoxy and/or halogen substituents;

$R^1$, $R^2$, $R^3$ and $R^{4'}$ are the same or different and are H, alkyl, a metal ion or a prodrug ester; and $R^5$ is H, halogen or lower alkyl; and $R^{15}$ is alkyl containing from 2 to 20 carbons;

the total nun%her of carbons in Zd exceeds 10.

9. The method as defined in claim 1, wherein the squalene synthetase inhibitor has the structure $$\begin{array}{c} O \quad Y^1 \quad O \\ \| \quad | \quad \| \\ R^1-(CH_2)_n-X-(CH_2)_m-P-C-P-OR^3 \\ | \quad | \quad | \\ OR^2 \quad Y^2 \quad OR^4 \end{array}$$

wherein m is 0, 1, 2 or 3; n is 0, 1, 2, 3 or 4;

$Y^1$ and $Y^2$ are H or halogen;

$R^2$, $R^3$ and $R^4$ may be the same or different and are independently H, metal ion, $C_1$ to $C_8$ alkyl or $C_3$ to $C_{12}$ alkenyl;

X is O, S, NH or $-NCH_2R^{15}$ wherein $R^{15}$ is H or $C_1$ to $C_5$ alkyl; and $R^1$ is $R^5-Q^1-Q^2-Q^3-$ wherein $Q^1$, $Q^2$ and $Q^3$ are the same or different and are independently $$\begin{array}{cc} R^7 \quad R^6 \quad R^8 & R^9 \\ | \quad | \quad | & | \\ -CH-C=C-CH_2-, & -CH_2-CH-CH_2-CH_2-, \end{array}$$

-continued

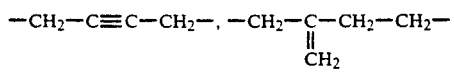

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl; $R^5$ is

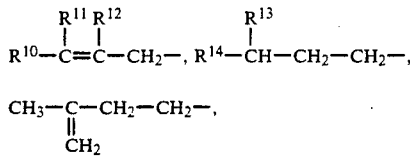

$CH_3(CH_2)_p$ where p is an integer from 2 to 7, or $R^{16}$—C≡C—$CH_2$— where $R^{16}$ is H or lower alkyl; $R^{10}$ $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$ $Q^2$ and $Q^3$ are bonds, then $R^{10}$ and $R^{11}$ cannot both be H, and $R^5$ cannot be $CH_3(CH_2)p$ with p less than or equal to 4, and when m is O, X is other than S; and if m is o and X is O, then n is 1, 2, 3 or 4; and including all stereoisomers thereof.

10. The method as defined in claim 1 wherein the squalene synthetase inhibitor has the structure $$R^1-(CH_2)_n-X-(CH_2)_m-\overset{\overset{O}{\|}}{\underset{\underset{OR^2}{|}}{P}}-\overset{\overset{Y^1}{|}}{\underset{\underset{Y^2}{|}}{C}}-\overset{\overset{O}{\|}}{\underset{\underset{OR^4}{|}}{P}}-OR^3$$

wherein m is 1, 2 or 3; n is 0, 1, 2, 3 or 4;
$Y^1$ and $Y^2$ are H or halogen;
$R^2$, $R^3$ and $R^4$ may be the same or different and are independently H, metal ion, $C_1$ to $C_8$ alkyl or $C_3$ to $C_{12}$ alkenyl;
X is O, S, NH or —$NCH_2R^{15}$ wherein $R^{15}$ is H or $C_1$ to $C_5$ alkyl; and
$R^1$ is $R^5$—$Q^1$—$Q^2$—$Q^3$— wherein $Q^1$, $Q^2$ and $Q^3$ are the same or different and are independently

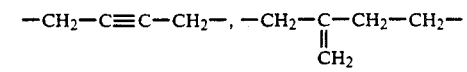

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl; $R^5$ is

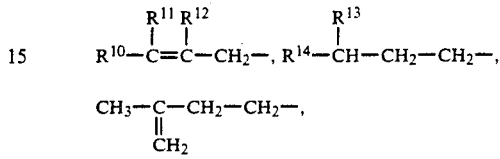

$CH_3(CH_2)_p$ where p is an integer from 2 to 7, or $R^{16}$—C≡C—$CH_2$— where $R^{16}$ is H or lower alkyl; $R^{10}$ and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; R is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then both $R^{10}$ and $R^{11}$ cannot be H, and $R^5$ cannot be $CH_3(CH_2)_p$ with a p less than or equal to 4, and including all stereoisomers thereof.

11. The method as defined in claim 1 wherein the squalene synthetase inhibitor has the structure

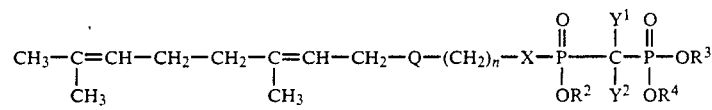

wherein Q is

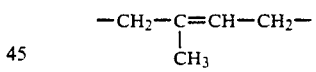

or a bond;
n is 0 to 4;
X is O, —NH— or $NCH_2R^{15}$;
$R^2$ $R^3$ and $R^4$ are the same or different and are H, lower alkyl, lower alkenyl, or a metal ion;
$Y^1$ and $Y^2$ may be the same or different and are H or halogen; and
$R^{15}$ is H or lower alkyl;
with the proviso that when X is O, n is 1, 2, 3, or 4.

12. The method as defined in claim 1 wherein the squalene synthetase inhibitor has the structure

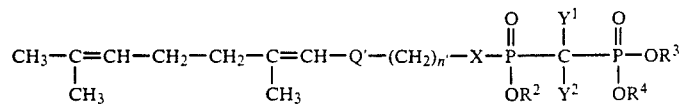

wherein Q' is

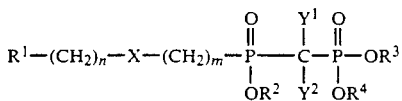

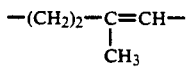

or a bond;

n' is 1, 2, 3 or 4;

X is O, —NH— or NCH$_2$R$^{15}$,

R$^2$, R$^3$ and R$^4$ are the same or different and are H, lower alkyl, lower alkenyl, or a metal ion;

Y$^1$ and Y$^2$ may be the same or different and are H or halogen; and

R$^{15}$ is H or lower alkyl;

with the proviso that when X is O, n' is 2, 3, or 4.

13. The method as defined in claim 1 wherein the squalene synthetase inhibitor has the structure

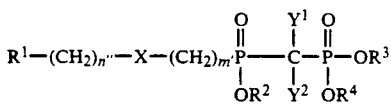

wherein m' is 1, 2 or 3; n" is 0, 1, 2 or 3;

Y$^1$ and Y$^2$ are H or halogen;

R$^2$, R$^3$ and R$^4$ may be the same or different and are independently H, metal ion, C$_1$ to C$_8$ alkyl or C$_3$ to C$_{12}$ alkenyl;

X is O, S, NH or —NCH$_2$R$^{15}$ wherein R$^{15}$ is H or C$_1$ to C$_5$ alkyl; and R$^1$ is R$^5$—Q$^1$—Q$^2$—Q$^3$— wherein Q$^1$, Q$^2$ and Q$^3$ are the same or different and are independently

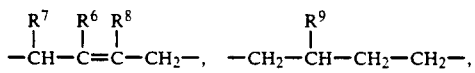

—CH$_2$—C≡C—CH$_2$—, or a single bond, with the proviso that if Q$^1$ is a bond, then Q$^2$ and Q$^3$ are bonds, and if Q$^2$ is a bond then Q$^3$ is a bond, and wherein R$^6$ is H, lower alkyl, halo or haloalkyl; R$^7$ is H, halogen, lower alkyl or lower alkylthio; R$^8$ is H, halogen, trimethylsilyl or lower alkyl; and R$^9$ is H or lower alkyl; R$^5$ is

CH$_3$(CH$_2$)$_p$ where p is an integer from 2 to 7, or R$^{16}$—C≡C—CH$_2$— where R$^{16}$ is H or lower alkyl; R$^{10}$, and R$^{11}$ are the same or different and are independently H, lower alkyl, haloalkyl, halogen or lower alkenyl or R$^{10}$ and R$^{11}$ can be taken together to form (CH$_2$)$_s$ where s is an integer from 2 to 7; R$^{12}$ is H, lower alkyl, halogen or lower alkenyl; and R$^{13}$ and R$^{14}$ are the same or different and are independently lower alkyl; with the proviso that if all of Q$^1$, Q$^2$ and Q$^3$ are bonds, then both R$^{10}$ and R$^{11}$ cannot be H, and R$^5$ cannot be CH$_3$(CH$_2$)$_p$ with a p less than or equal to 4, and including all stereoisomers thereof.

14. The method as defined in any of claim 1 wherein the squalene synthetase inhibitor has the formula

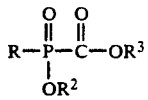

wherein R$^2$ is a metal ion lower alkyl or H; R$^3$ is a metal ion or lower alkyl; R is R$^1$—(CH$_2$)$_n$—, R$^1$—(CH$_2$)$_m$O— or R$^1$(CH$_2$)$_m$OCH$_2$—, wherein n is an integer from 1 to 4 and m is an integer from 0 to 3; and R$^1$ is R$^5$—Q$^1$—Q$^2$—Q$^3$— wherein Q$^1$, Q$^2$ and Q$^3$ are independently:

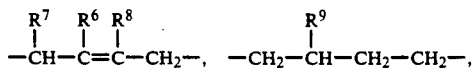

—CH$_2$—C≡C—CH$_2$—, or a bond, with the stipulation that if Q$^1$ is a bond, then Q$^2$ and Q$^3$ must be bonds, and if Q$^2$ is a bond, then Q$^3$ is a bond; R$^6$ is H, lower alkyl fluoro or fluoroalkyl; R$^7$ is H, fluoro, lower alkyl or alkylthio; R$^8$ is H, fluoro, trimethylsilyl or lower alkyl; R$^9$ is H or lower alkyl; R$^5$ is

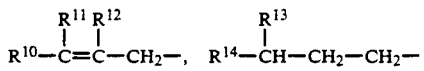

R$^{16}$—C≡C—CH$_2$— (wherein R$^{16}$ is lower alkyl or H), or CH$_3$(CH$_2$)$_p$— where p is 2 to 7; R$^{10}$ and R$^{11}$ are independently hydrogen, lower alkyl, fluoro, lower alkenyl or fluoroalkyl or R$^{10}$ and R$^{11}$ can be taken together to form (CH$_2$)$_s$, where s is 2 to 7; R$^{12}$ is hydrogen, lower alkyl fluoro or lower alkenyl; R$^{13}$ and R$^{14}$ are independently lower alkyl; with the proviso that if all of Q$^1$, Q$^2$ and Q$^3$ are bonds, then R$^{10}$ and R$^{11}$ cannot both be H, and R$^5$ cannot be CH$_3$(CH$_2$)$_p$, with p≦4, including all stereoisomers thereof.

15. The method as defined in claim 1 wherein the squalene synthetase inhibitor has the structure

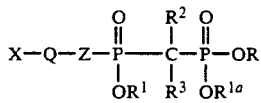

wherein Q is

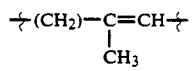

or a bond;

Z is —(CH$_2$)$_n$— or —(CH$_2$)$_p$—CH=CH—(CH$_2$)$_m$—, wherein n is 1 to 5; p is 0, 1 or 2; m is 0, 1 or 2;

R, R$^1$ and R$^{1a}$ are the same or different and are H, lower alkyl or a metal ion;

R$^2$ and R$^3$ may be the same or different and are H or halogen; and X is

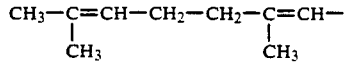

16. The method as defined in claim 1 wherein the squalene synthetase inhibitor has the structure $$CH_3-\underset{CH_3}{\underset{|}{C}}=CH-CH_2-CH_2-\underset{CH_3}{\underset{|}{C}}=CH-(CH_2)_2-\underset{CH_3}{\underset{|}{C}}=CH-(CH_2)_n-\underset{OR^1}{\overset{O}{\underset{||}{P}}}-\underset{R^3}{\underset{|}{C}}-\overset{R^2}{\underset{OR^{1a}}{\overset{|}{P}}}-OR,$$

$$CH_3-\underset{CH_3}{\underset{|}{C}}=CH-CH_2-CH_2-\underset{CH_3}{\underset{|}{C}}=CH-(CH_2)_n-\underset{OR^1}{\overset{O}{\underset{||}{P}}}-\underset{R^3}{\underset{|}{C}}-\overset{R^2}{\underset{OR^{1a}}{\overset{|}{P}}}-OR,$$

$$CH_3-\underset{CH_3}{\underset{|}{C}}=CH-CH_2-CH_2-\underset{CH_3}{\underset{|}{C}}=CH-(CH_2)_2-\underset{CH_3}{\underset{|}{C}}=CH-(CH_2)_p-CH=CH-(CH_2)_m-\underset{OR^1}{\overset{O}{\underset{||}{P}}}-\underset{R^3}{\underset{|}{C}}-\overset{R^2}{\underset{OR^{1a}}{\overset{|}{P}}}-OR$$

or $$CH_3-\underset{CH_3}{\underset{|}{C}}=CH-CH_2-CH_2-\underset{CH_3}{\underset{|}{C}}=CH-(CH_2)_p-CH=CH-(CH_2)_m-\underset{OR^1}{\overset{O}{\underset{||}{P}}}-\underset{R^3}{\underset{|}{C}}-\overset{R^2}{\underset{OR^{1a}}{\overset{|}{P}}}-OR$$

17. The method as defined in claim 1 wherein the squalene synthetase inhibitor has the structure $$R^2-\underset{R^3O}{\overset{O}{\underset{||}{P}}}-\underset{R^1}{\overset{Z}{\underset{|}{C}}}-\underset{OR^4}{\overset{O}{\underset{||}{S}}}=O$$

wherein $R^2$ is $OR^5$ or $R^{5a}$, $R^3$ and $R^5$ are independently H, alkyl, arylalkyl, aryl, cycloalkyl, metal ion or other pharmaceutically acceptable salt, or prodrug ester;

$R^{5a}$ is H, alkyl, arylalkyl or aryl;

$R^4$ is H, alkyl, aryl, cycloalkyl, arylalkyl, metal ion, or other pharmaceutically acceptable salt, or prodrug ester;

$R^1$ is a lipophilic group containing at least 7 carbons;

Z is H, halogen, lower alkyl or lower alkenyl.

18. The compound as defined in claim 17 wherein $R^1$ is alkyl containing 7 to 25 carbons in the chain; alkenyl containing from 7 to 25 carbon atoms in the chain and from 1 to 6 double bonds; alkynyl containing 1 to 6 triple bonds; mixed alkenylalkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; or a group of the structure $$\underset{R^8}{\overset{R^6}{\diagdown}}Ar-(CH_2)_{p''} \diagdown R^{8a}$$

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloalkylalkyl, Ar-alkyl, ArO, Ar-amino, Ar, Ar-thio, Ar-sulfinyl, Ar-sulfonyl, cyano, Ar-carbonyloxy, or Ar-carbonylamino.

19. The method as defined in claim 1 wherein the squalene synthetase inhibitor has the structure $$H-\underset{R^2O}{\overset{O}{\underset{||}{P}}}-\underset{R^1}{\overset{H}{\underset{|}{C}}}-\underset{OR^4}{\overset{O}{\underset{||}{P}}}-OR^3$$

wherein $R^2$, $R^3$ and $R^4$, are independently H, alkyl, a metal ion or a prodrug ester; and $R^1$ is a lipophilic group containing at least 6 carbons, and including pharmaceutically acceptable salts thereof.

20. The compound as defined in claim 19 wherein $R^1$ is alkyl, alkenyl, alkynyl or aryl.

* * * * *